US00PP21090P2

(12) United States Plant Patent
Saul

(10) Patent No.: US PP21,090 P2
(45) Date of Patent: Jun. 22, 2010

(54) *BRASSICA* PLANT NAMED 'KALEIDOSCOPE'

(50) Latin Name: *Brassica oleracea*
Varietal Denomination: Kaleidoscope

(75) Inventor: Richard G. Saul, Cleveland, GA (US)

(73) Assignee: Itsaul Plants, LLC, Alpharetta, GA (US)

( * ) Notice: Subject to any disclaimer, the term of this patent is extended or adjusted under 35 U.S.C. 154(b) by 0 days.

(21) Appl. No.: 12/378,829

(22) Filed: Feb. 20, 2009

(51) Int. Cl.
*A01H 5/00* (2006.01)

(52) U.S. Cl. ..... Plt./373

(58) Field of Classification Search ..... Plt./373, Plt./263.1
See application file for complete search history.

*Primary Examiner*—June Hwu
(74) *Attorney, Agent, or Firm*—Penny J Aguirre

(57) ABSTRACT

A new cultivar of hybrid *Brassica*, 'Kaleidoscope', characterized by its dark purple-green foliage with highly ruffled edges, its magenta pink veins and its margins that are magenta pink in color when grown under cool temperature and lavender in color when grown under warm temperatures such as early season growth.

2 Drawing Sheets

Botanical classification: *Brassica oleracea.*
Cultivar designation: 'Kaleidoscope'.

BACKGROUND OF THE INVENTION

The present invention relates to a new and distinct cultivar of hybrid Ornamental Kale, botanically known as *Brassica oleracea* 'Kaleidoscope' and will be referred to hereafter by its cultivar name, 'Kaleidoscope'. The new cultivar represents a new Ornamental Kale, a plant grown as an annual for fall landscape use as a container and bedding plant.

The Inventor discovered the new cultivar, 'Kaleidoscope', in his nursery in Dahlonega, Ga. in the autumn of 2007. 'Kaleidoscope' was discovered as a single unique plant in a one-gallon container in a block of containers planted with seed of *Brassica oleracea* 'Redbor Kale' (not patented).

Asexual reproduction of the new cultivar was first accomplished by the Inventor using stem cuttings in Dahlonega, Ga., in November of 2007. The characteristics of this cultivar have been determined to be stable and are reproduced true to type by both in-vitro propagation and cutting production in successive generations.

SUMMARY OF THE INVENTION

The following traits have been repeatedly observed and represent the characteristics of the new cultivar. These attributes in combination distinguish 'Kaleidoscope' from other varieties of *Brassica oleracea* known to the Inventor.

1. 'Kaleidoscope' exhibits purple-green foliage with highly ruffled edges.
2. The foliage of 'Kaleidoscope' is variegated with margins that are magenta pink in color when grown under cool temperature and lavender in color when grown in warm temperatures such as early season growth.
3. The foliage of 'Kaleidoscope' exhibits veins that are magenta pink in color.

'Kaleidoscope' differs from the parent plant, 'Redbor' by having marginal variegation that is magenta pink in color. The foliage of 'Redbor' is solid purple-green in color and lacks the magenta colored margins. 'Kaleidoscope' has a similar growth habit, ruffled leaf margins and vein color to 'Redbor'. 'Kaleidoscope' can also be compared to 'Winterbor' (not patented), 'Winterbor' has a similar growth habit however the foliage of 'Winterbor' is medium green in color.

BRIEF DESCRIPTION OF THE DRAWING

The accompanying colored photographs were taken in September of 11 month-old plants of 'Kaleidoscope' and illustrate the overall appearance and distinct characteristics of the new Ornamental Kale.

The photograph in FIG. 1 shows six plants of 'Kaleidoscope' as planted in the landscape with the center foliage characteristic of the foliage when grown under cool temperatures.

Figure 1:
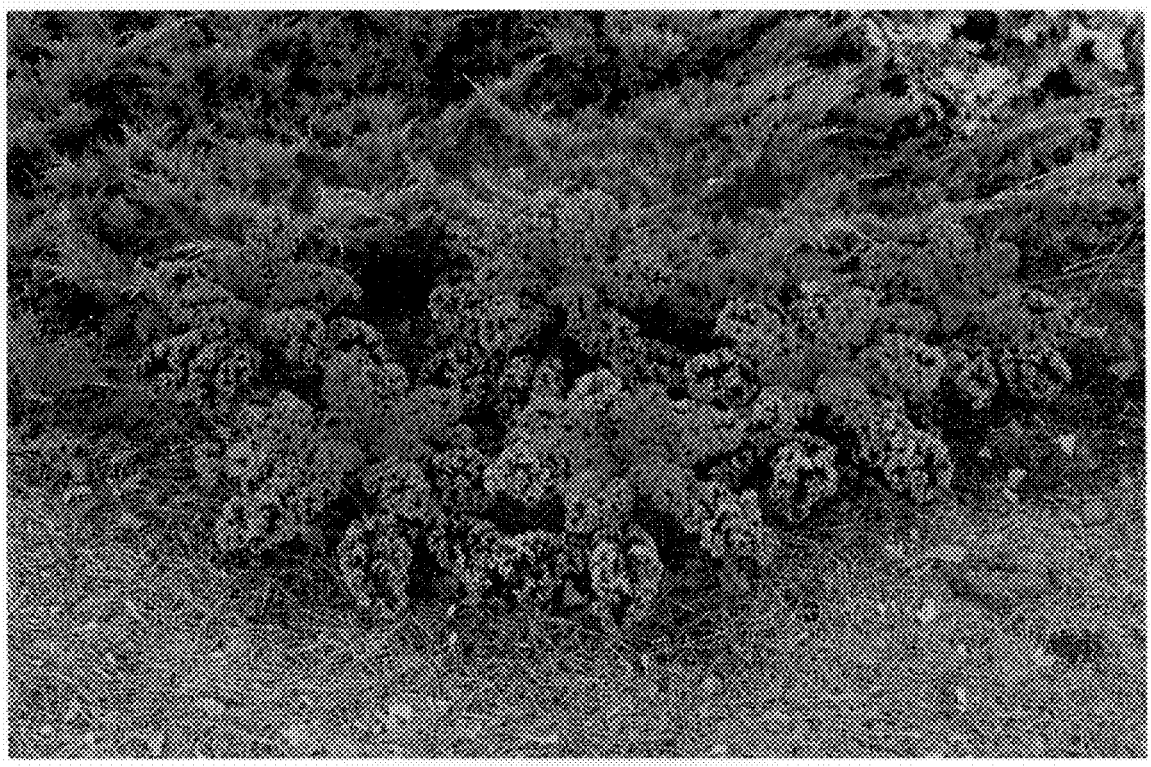
Figure 2:
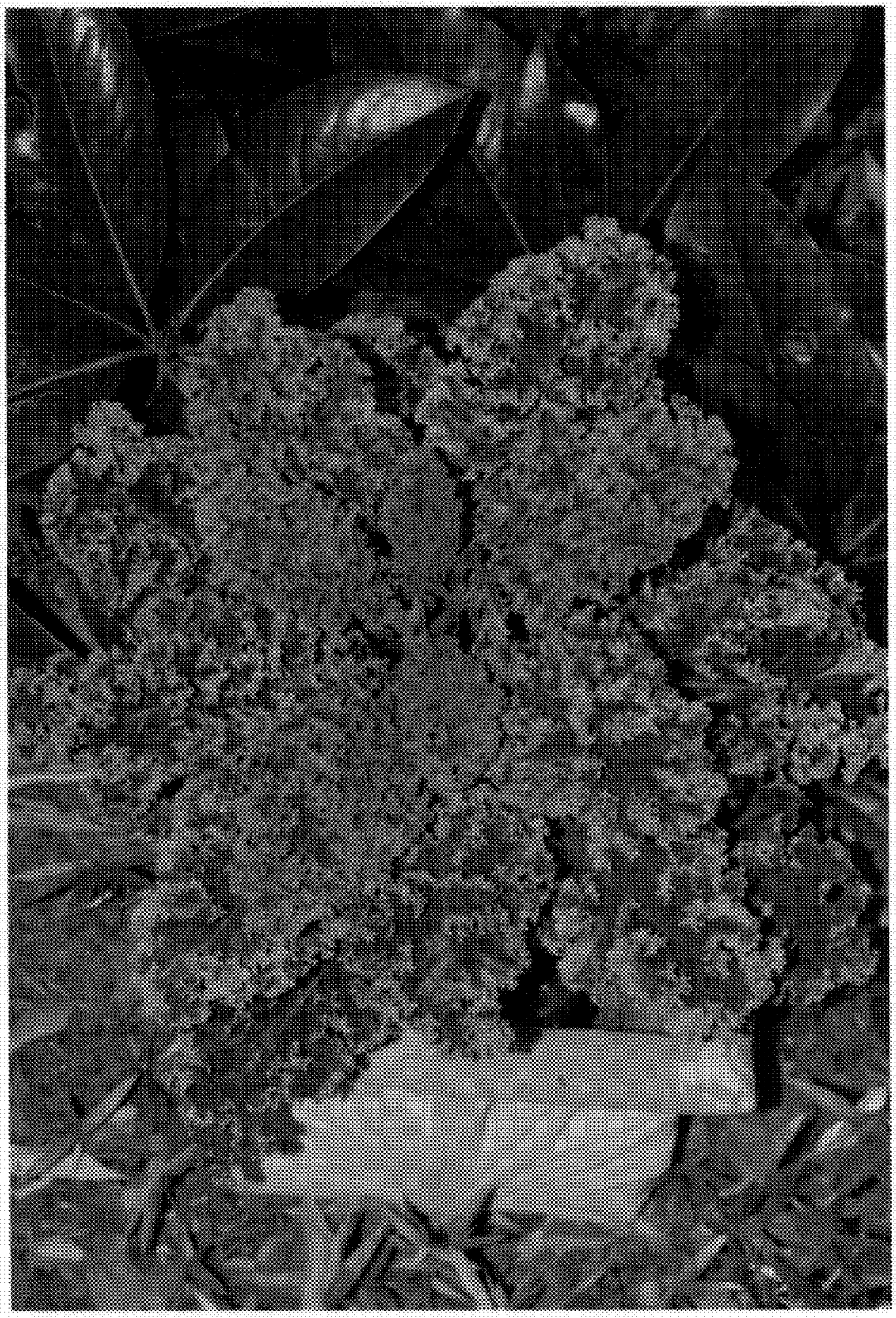

The photograph in FIG. 2 is a view of a plant of 'Kaleidoscope' as grown in a one-gallon container.

The colors in the photograph may differ slightly from the color values cited in the detailed botanical description, which accurately describe the colors of the new Ornamental Kale.

DETAILED BOTANICAL DESCRIPTION OF THE PLANT

The following is a detailed description of 6 month-old plants of the new cultivar as grown outdoors in one-gallon containers under natural light in Dahlonega, Ga. Leaf data was also collected from younger 2 month-old plants as grown under plastic cover in one-gallon containers at a minimum 40° F. night temperature (cool temperatures) in Dahlonega, Ga. and provide. The phenotype of the new cultivar may vary with variations in environmental, climatic, and cultural conditions, as it has not been tested under all possible environmental conditions. The color determination is in accordance with the 2007 R.H.S. Color Chart of The Royal Horticultural Society, London, England, except where general color terms of ordinary dictionary significance are used.

General description:

*Blooming period.*—Flowers not observed.

*Plant type.*—Herbaceous biennial, grown as an annual.

*Plant habit.*—Upright.

*Height and spread.*—Reaches about 38 cm in width and about 60 cm in height.

*Hardiness.*—Grown as a fall ornamental (single season use).

*Culture.*—Grows best in full sun in constantly moist, well-drained soils of neutral pH, performs best in the cool weather temperatures of autumn.

*Diseases and pests.*—No increased susceptibility or resistance to diseases or pests common to Ornamental Kale has been observed.

*Root description.*—Fibrous.

Growth and propagation:

*Propagation.*—In vitro propagation is the preferred method, cuttings are also possible.

*Root development from cuttings.*—Roots appear in 7 to 10 days in the fall and winter from cuttings dipped with a rooting hormone in a 70° F. greenhouse without supplemental lighting, rooted cuttings finish a 72-cell plug in about 4 to 5 weeks.

*Root development from in vitro propagation.*—Roots initiate in about 2 weeks from plants propagated in-vitro under laboratory conditions of 16 hour lighting at 73° F. and finish a 72-cell plug in about 5 weeks.

*Growth rate.*—Vigorous.

Stem description:

*Stem size.*—Up to 60 cm in length, about 1.5 cm in width, strong.

*Stem aspect.*—Upright.

*Stem shape.*—Oval with some ridges.

*Stem color.*—79A to 79B (cool temperature), 77A (warm temperatures).

*Stem surface.*—Glaucous to pruinose.

*Branching.*—Single stem.

Foliage description:

*Leaf shape.*—Obovate and lyrate.

*Leaf division.*—Primarily simple with a few, small alternate leaflets occurring at the base of the leaf, basal leaflets are similar in characteristics to leaf lobes and an average of 1 cm in length and 6 mm in width.

*Leaf base.*—Cuneate.

*Leaf apex.*—Rounded to obtuse.

*Leaf venation.*—Pinnate, upper surface; N81A in color, glossy, lower surface; 79A to 79B in color, glaucous, prominent, raised, warm early season growth; 72A on upper surface and 77A on lower surface.

*Leaf margins.*—Incised to laciniate, extremely ruffled, wavy, leaf segments deeply divided with center sinuses up to 5.5 cm in length and apex sinuses about 1 cm in length.

*Leaf attachment.*—Petiolate.

*Leaf arrangement.*—Alternate to spiral.

*Leaf surface.*—Rubbery, upper surface; slightly glossy, lower surface glaucous.

*Leaf color mature plant* (*cool temperatures*).—Upper surface; emerge 71A becoming N92A blended with 147A with marginal variegation 2 mm to 14 mm in length of N80B to N81B, maturing to 83A blended with 147A with marginal variegation of 83D, lower surface; emerge 59A becoming 189A with marginal variegation 81C, maturing to 79B with marginal variegation of 79D.

*Leaf color of early season growth* (*warm temperatures*).—Upper surface; emerge 70A becoming 147A with marginal variegation 1 mm to 5 mm in length 70A, matures to 147A with marginal variegation 1 mm to 12 mm in length of 75A to 75B to 76A, lower surface; emerging leaves 71A becoming 146C to 146D with marginal variegation of 70A to 71B, mature to 148A with marginal variegation of 75A to 76B.

*Leaf size.*—Average of 18.5 cm in length and 9.5 cm in width.

*Leaf quantity.*—Average of 55 leaves per plant.

*Leaf durability to stress.*—High.

*Leaf aspect.*—Newly expanded leaves held at a nearly 45° angle, mature to an arching aspect, old mature leaves curl downward, variegated leaf margins are extremely ruffled, curled, and draw the marginal edge inward, bisecting the midrib in portions of some leaves.

*Petioles.*—Average of 3 to 5 cm in length and an average of 7 mm at attachment to stem, 3.5 mm at beginning of leaf blade and 3 mm in width (triangular in shape), N81A in color (N81B in warm temperatures), surface is glabrous to slightly glaucous.

Flower description: Flowers have not been observed, as plants are grown as annual for its foliage.

*Fruit and seed.*—None.

It is claimed:

1. A new and distinct cultivar of *Brassica* plant named 'Kaleidoscope' as herein illustrated and described.

* * * * *